United States Patent
Foglia et al.

(10) Patent No.: US 10,159,245 B2
(45) Date of Patent: Dec. 25, 2018

(54) DEVICE FOR THE HANDLING AND TRANSPORTATION OF AN EYEBALL

(71) Applicant: Roberta Foglia, Pazzallo-lugano (CH)

(72) Inventors: Roberta Foglia, Pazzallo-lugano (CH); Carmelo Foglia, Pazzallo-lugano (CH)

(73) Assignee: Roberta Foglia, Pazzallo-Lugano (CH)

( * ) Notice: Subject to any disclaimer, the term of this patent is extended or adjusted under 35 U.S.C. 154(b) by 4 days.

(21) Appl. No.: 15/107,135

(22) PCT Filed: Dec. 22, 2014

(86) PCT No.: PCT/IB2014/067216
§ 371 (c)(1),
(2) Date: Jun. 22, 2016

(87) PCT Pub. No.: WO2015/097638
PCT Pub. Date: Jul. 2, 2015

(65) Prior Publication Data
US 2016/0338345 A1    Nov. 24, 2016

(30) Foreign Application Priority Data

Dec. 23, 2013  (IT) .............................. RM2013A0713

(51) Int. Cl.
*A01N 1/02*  (2006.01)
*A61F 2/14*  (2006.01)

(52) U.S. Cl.
CPC .................................. *A01N 1/0273* (2013.01)

(58) Field of Classification Search
CPC ......... A01N 1/0273; A01N 1/02; A61F 2/141; A61F 2/0095

USPC ....................................................... 435/284.1
See application file for complete search history.

(56) References Cited

U.S. PATENT DOCUMENTS

| | | | | |
|---|---|---|---|---|
| 2,880,856 A * | 4/1959 | Albrecht | ................... | A01N 1/02 206/205 |
| 5,077,218 A * | 12/1991 | Marquette | ............ | A01N 1/0273 422/547 |
| 5,586,438 A * | 12/1996 | Fahy | ........................ | A01N 1/02 435/284.1 |
| 6,394,604 B1 * | 5/2002 | Bentley | ...................... | A61F 2/14 351/245 |
| 2011/0008877 A1 * | 1/2011 | Skelnik | ................ | A01N 1/0263 435/284.1 |
| 2013/0157249 A1 * | 6/2013 | Ilyin | ...................... | A01N 1/021 435/2 |

(Continued)

OTHER PUBLICATIONS

Francisco Figueiredo: "Standards for the Retrieval of Human Ocular Tissue Used in Transplantation, Research and Training", Jul. 1, 2013 (Jul. 1, 2013), pp. 1-20, XP055115550.

(Continued)

*Primary Examiner* — Kevin Joyner
*Assistant Examiner* — Holly M Mull
(74) *Attorney, Agent, or Firm* — Young & Thompson

(57) ABSTRACT

A device (10) is provided for the handling and transportation of an eyeball (1) including: at least one base body (2) including a first housing seat or cavity (4) for housing at least partially the eyeball; at least one retaining element (3) including at least three fins (13) for retaining the eyeball in the first housing seat or cavity; and at least one lid (5) removably combinable with the base body.

22 Claims, 7 Drawing Sheets

(56) References Cited

U.S. PATENT DOCUMENTS

2013/0295673 A1* 11/2013 Taghizadeh ............ C12M 45/02
  435/379
2016/0029618 A1* 2/2016 Gain .................... A01N 1/0247
  435/284.1

OTHER PUBLICATIONS

Jan Schroeter et al.: "Comparison of in situ Corneoscleral Disc Excision versus Whole Globe Enucleation in Cornea Donors Regarding Microbial Contamination in Organ Culture Medium—a Prospective Monocentric Study over 9 Years", Transfusion Medicine and Hemotherapy, vol. 39, No. 6, Jan. 1, 2012 (Jan. 1, 2012), pp. 391-394, XP055115552, ISSN: 1660-3796.
Kim J H et al.: "Comparison of In Situ Excision and Whole-Globe Recovery of Corneal Tissue in a Large, Single Eye Bank Series", American Journal of Ophthalmology, Elsevier, Amsterdam, NL, vol. 150, No. 3, Sep. 1, 2010 (Sep. 1, 2010), pp. 427-433.e1, XP027232756, ISSN: 0002-9394.
International Search Report, dated Apr. 20, 2015, from corresponding PCT application.

* cited by examiner

DEVICE FOR THE HANDLING AND TRANSPORTATION OF AN EYEBALL

DESCRIPTION

The present invention concerns the field of preservation, transportation and processing of eyeballs to be prepared for corneal transplantation, more particularly the present invention concerns a device for the handling and transportation of an eyeball.

KNOWN ART

Currently, in hospitals or specialized medical centers, the preservation and processing procedure of an eyeball to be prepared for corneal transplantation provides for the eyeball, once explanted, to be wound at its base by gauzes soaked with saline solution, whereas the apical part, where the cornea is, is kept free.

The eyeball is then inserted in a glass or receptacle, not specific for the purpose (for example, that one for collecting the urine or the like), containing a first transportation liquid. The receptacle is then closed by the respective lid.

The Applicant observed that the function of the gauzes soaked with saline solution is to support the eyeball, thereby avoiding the same to be overturned in the glass full of liquid, so as to avoid corneal damages.

However, the Applicant observed that this method is not effective in maintaining the eyeball in the desired position and then it does not prevent corneal damages, most of all during transportation.

After the receptacle or glass have been positioned, the eyeball is preserved in a refrigerator for a short time, awaiting observation and processing procedures or the successive transportation to specialized facilities.

During the observation and processing procedures, the eyeball is drawn out from the glass and positioned in another second small receptacle to allow the cornea to be observed by the microscope, the small receptacle containing an appropriate second processing liquid.

The second receptacle, currently used for the microscope observation, is smaller than the receptacle for the transportation, so that it can be positioned on the microscope and the corneal endothelium can be subsequently focused. This receptacle is provided with a lid having a central circular opening, at the cornea.

Then the Applicant observed that, at the moment, two different receptacles are needed for the transportation and then for the microscope observation of the eyeball.

If the cornea is suitable for the transplantation, the separation of the cornea from the eyeball will be needed through a circular cut not many millimeters far away from the limbus.

At the moment, the eyeball is left in the second receptacle for the corneal cutting, but without the lid.

The Applicant still observed that this procedure is inconvenient since the eyeball, during the cutting, tends to slid, as it has nothing for its securing to the second receptacle. The cutting is also inconvenient by keeping the eyeball in one hand, as also in this way the eyeball tends to slide.

After the cutting step, the corneal preparation, i.e. the cornea extracted from the eyeball, is inserted into a third receptacle containing a third liquid, suitable for a longer preservation, awaiting for the transplantation. The rest of the eyeball and the first receptacle are eliminated, whereas the second receptacle to be microscope observed is sterilized for its reuse.

The Applicant still observed that the sterilization operations of the second receptacle involve costs and additional processes for operators assigned to such tasks.

Furthermore, the Applicant observed that hospitals not performing corneal transplantations, after the explantation, must send the eyeballs as soon as possible to a specialized center for observation and processing procedures.

Currently, eyeballs are sent inside the above mentioned glasses (sterile glasses for collecting urine or the like) in the appropriate transportation liquid, and are wound by gauzes in order to stabilize the eyeball itself, with the cornea facing upwards and then contacting only the transportation liquid.

However, this method has the risk of overturning the eyeball during transportation, with a possible consequent corneal damage.

Then the Applicant found the need of providing a device for the handling and transportation of an eyeball, which allows the problems of the known art to be eliminated or anyway appreciably reduced. In particular, it allows the risk of a possible corneal damage, due to the transportation, to be reduced or eliminated, and it allows the eyeball to be kept in a fixed position during the observation and processing procedures.

Furthermore, the Applicant found the need of providing a device for the handling, transportation, observation and processing of an eyeball, which reduces the number of receptacles for the above described different steps and reduces the impact related to sterilizing operations in terms of costs and processing. The novel device is, as a matter of fact, "disposable" and consists of a receptacle suitable for the transportation and a second receptacle suitable, which is already incorporated, for the microscope observation. Through this method the eyeball displacements from one receptacle to another are eliminated, so as to reduce manipulations.

SUMMARY OF THE INVENTION

Therefore, in its first aspect the invention refers to a device for the handling, transportation, observation and processing of an eyeball for corneal transplantation or research, comprising:
- at least one base body comprising a first housing seat or cavity extending around a substantially vertical axis for housing at least partially an eyeball;
- at least one retaining element for retaining the eyeball in said first housing seat or cavity; said retaining element comprising a plurality of fins, comprising at least three fins which are arranged around said first housing seat or cavity; said fins being shaped so as to contact the eyeball for at least 15% of an ocular circumference obtained by the intersection between a plane orthogonal to the vertical axis of said first housing seat or cavity and the eyeball itself;
- at least one lid removably combinable with the base body.

The device according to the present invention allows obtaining a greater stability of the eyeball and a support for a higher safety and, consequently, maintaining of the corneal integrity both during transportation and during the preservation in a refrigerator.

Furthermore, the device according to the present invention is also suitable for the microscope observation and the corneal cutting, since an excellent fastening of the eyeball, with no sliding during the circular cutting, is allowed thanks to the housing cavity and the retaining element which directly support and retain the eyeball.

In fact, the Applicant found that the eyeball can be kept in position by retaining it in at least three distinct contact zones, most of all during the corneal cutting. In fact, a smaller number of contact zones would not be sufficient to retain the eyeball in position, which would slide and risk irreparable damages to the cornea. In fact, during this operation, the eyeball is urged in different directions by scalpels or cutting tools, then the retaining element must be able to counter every stress, most of all lateral, which could come from any direction useful for the corneal cutting.

Moreover, the Applicant found that the contact surface between the retaining element and the eyeball must be extended beyond a specified minimum zone so that the eyeball itself is not damaged, in particular due to the unpredictability of direction stresses to which the eyeball itself is subjected during the corneal cutting.

In the scope of the present invention:
with "axial direction" or "axially", a direction coincident or parallel to the vertical symmetry axis of the device is meant, the vertical symmetry axis being shown with X-X in figures;
with "radial direction" or "radially", a direction generally moving away from the vertical symmetry axis of the device, is meant;
with "circumferential direction", a direction along a circumference having its center along a straight line coincident or parallel to the vertical symmetry axis of the device, is meant.

In the above said aspect, the present invention may have at least one of the hereinafter described characteristics.

Preferably, the at least three fins are angularly spaced.

Preferably, the fins are shaped so as to contact the eyeball for at least 40% of the ocular circumference.

Conveniently, the base body comprises a seat adapted to accommodate the stump of the visual nerve, preferably in communication with the afore said housing cavity.

Advantageously, the retaining element can be removably fastened to the base body through first removable coupling means.

Conveniently, the cavity comprises a maximum diameter Dmax and said retaining element comprises at least two portions arranged for defining a diameter shorter than said maximum diameter Dmax of said cavity.

Preferably, the lid combined with the base body makes a cavity for a preservation and/or transportation liquid.

Conveniently, the lid is combined with the base body through second releasable coupling means.

Advantageously, the cavity for the transportation liquid is hermetically sealed.

Preferably, the lid comprises a first opening for the fluidic communication of the cavity with the outside and at least one plug for closing the afore said first opening hermetically and removably.

Conveniently, the cavity comprises a volume between 10 and 100 milliliters.

Advantageously, the first housing seat or cavity for housing at least partially said eyeball has a sphere shape or a sphere-portion shape, or else a conical shape.

Preferably, the seat for the eyeball stump is arranged at a bottom end of said cavity for housing at least partially said eyeball.

Conveniently, the base body is composed of two pieces that can be removably combined by third coupling means.

Advantageously, the device according to the present invention comprises constraining means for fastening said base body to a bearing surface.

Preferably, the retaining element comprises a crown wheel comprising a plurality of fins that are circumferentially arranged around said first housing seat or cavity for housing at least partially said eyeball.

Preferably, the retaining element comprises an annular contacting element adapted to join said fins and to contact the eyeball.

Conveniently, said fins of said retaining element are elastically deformable.

Preferably, said retaining element can be adjustably combined with said base body.

Conveniently, the device according to the invention comprises a ring nut comprising an opening for housing at least one portion of the eyeball containing the cornea; said ring nut being removably combinable with said base body.

Advantageously, said ring nut comprises removable fastening means for the fastening to said base body and at least one tank for a preservation liquid, the tank having a shape adapted to house at least partially the cornea.

Preferably, said ring nut is combinable with said upper portion of the base body through said removable fastening means.

Advantageously, said ring nut combined with said upper portion of said base body comprises a maximum height ($H_{max}$) lower or equal to 50 mm.

BRIEF DESCRIPTION OF THE DRAWINGS

Further characteristics and advantages of the invention will be more evident from the detailed description of some preferred embodiments, but not exclusive, of a device for the handling and transportation of an eyeball according to the present invention.

Such a description will be hereinafter explained referring to the attached drawings, provided for purposes of illustrations only, and thereby not limitative, wherein.

DETAILED DESCRIPTION OF EMBODIMENTS OF THE INVENTION

Figure 1:
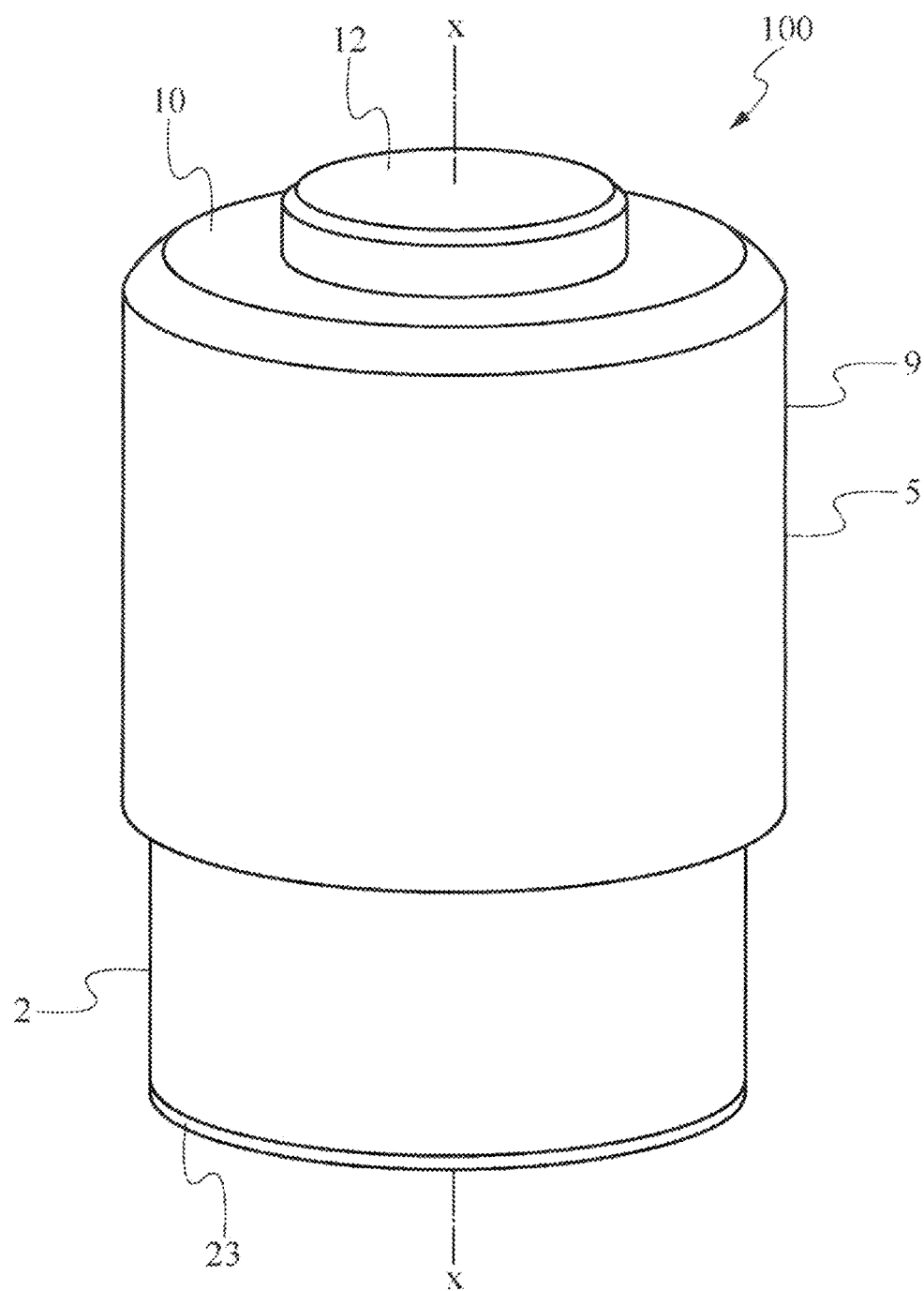
FIG. 1 is a schematic perspective view of a first embodiment of a device for the handling and transportation of an eyeball according to the present invention.
Figure 2:
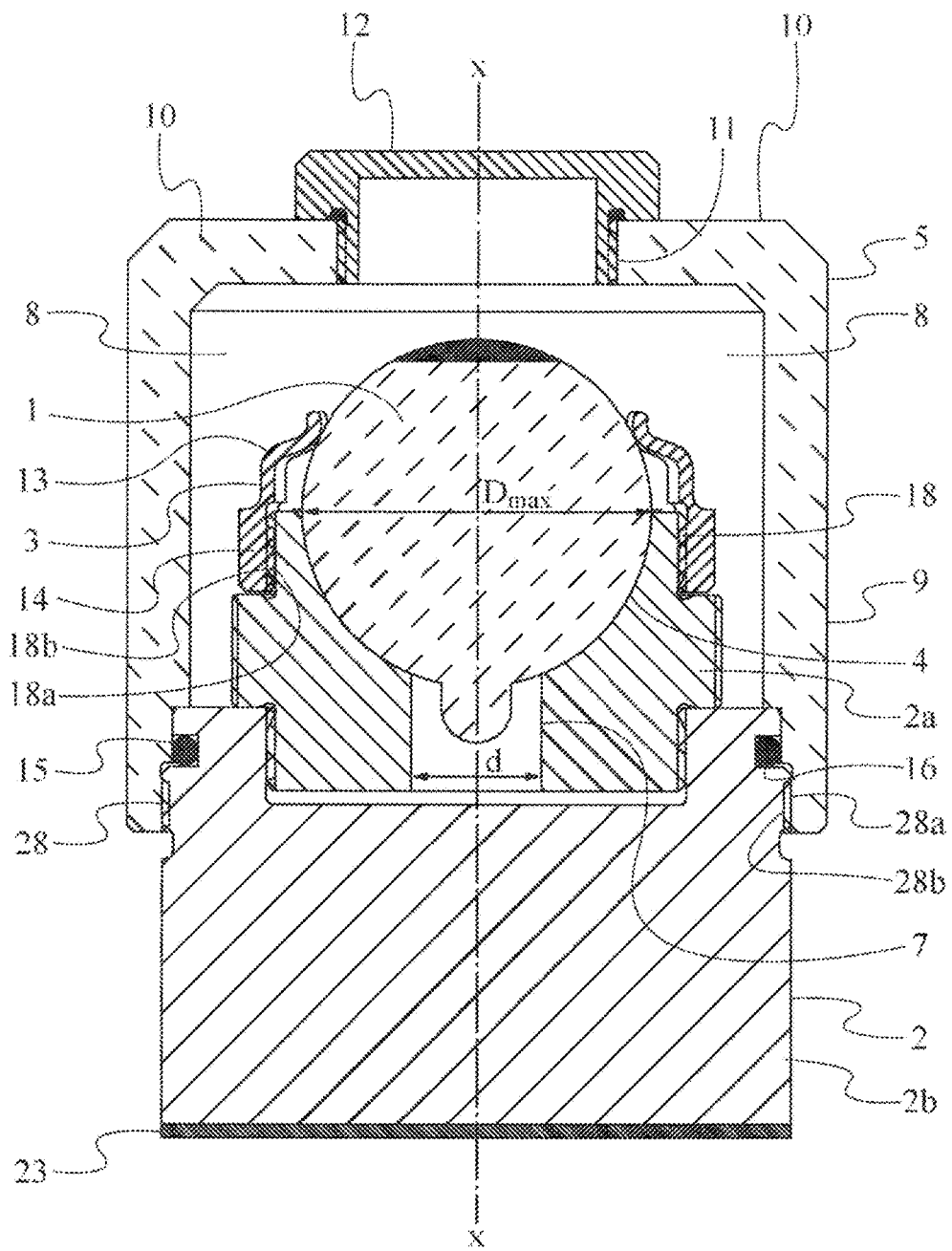
FIG. 2 is a schematic sectional view of the device for the handling and transportation of an eyeball shown in FIG. 1.
Figure 3:
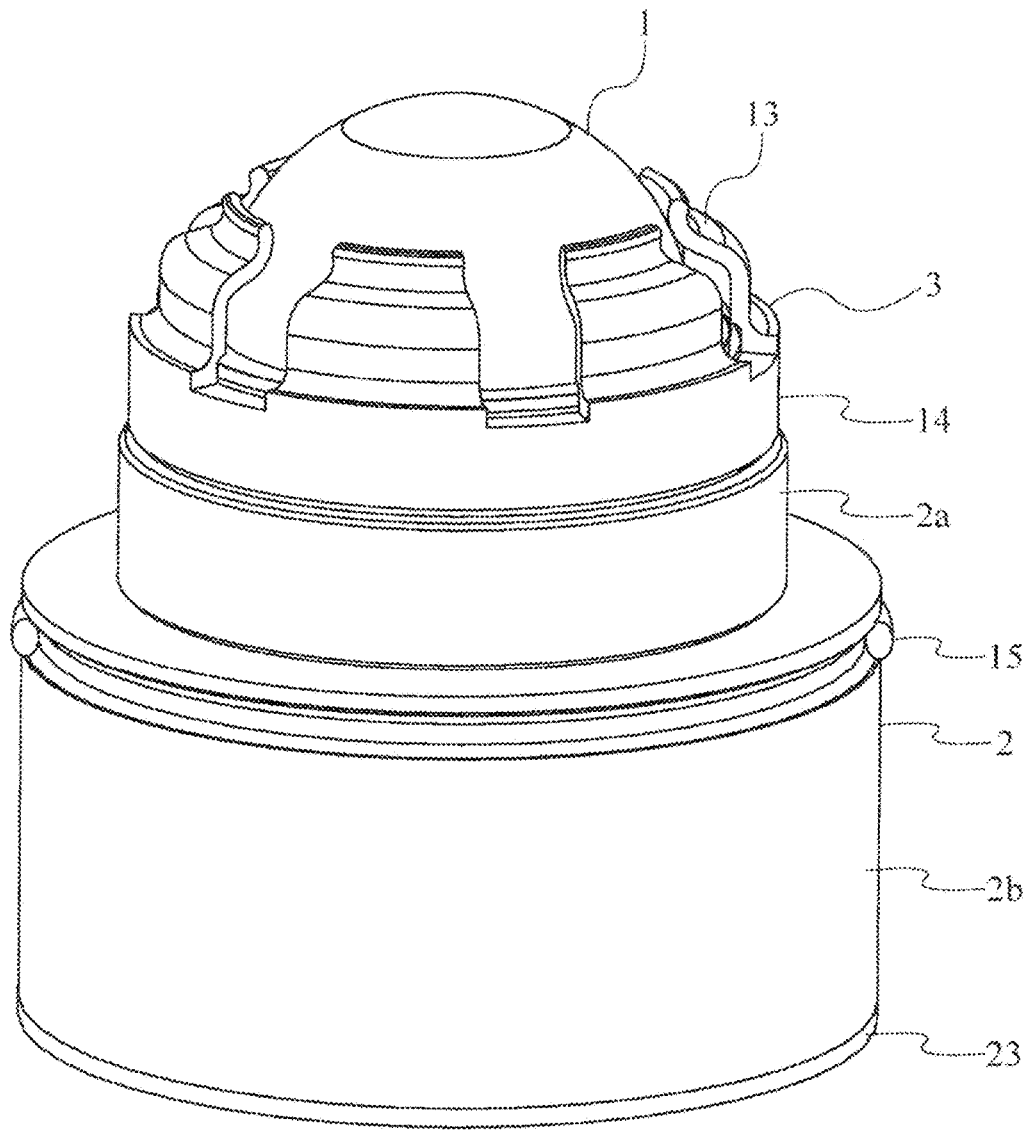
FIG. 3 is a schematic perspective view of the device for the handling and transportation of an eyeball shown in FIG. 1, in which the lid 5 has been removed.

Referring to FIGS. 1-3, a device for the handling, transportation, observation and processing of an eyeball according to the present invention, is identified with reference numeral 10.

Figure 4:
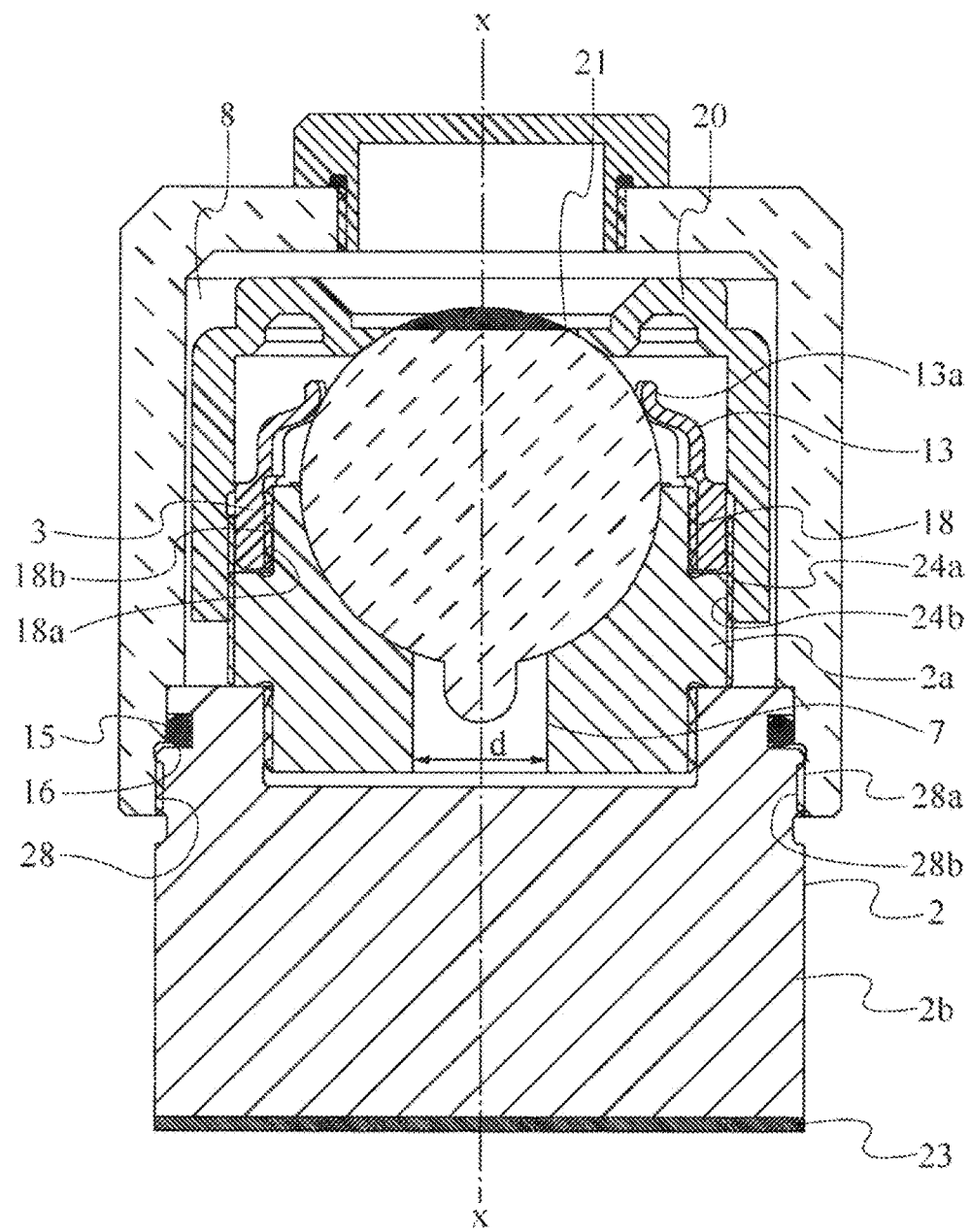
FIG. 4 is a schematic sectional view of the device of FIG. 1 with the ring nut combined with the upper portion of the base body.

In the embodiment shown in FIGS. 1-4 and in particular in FIGS. 2 and 4, the device 10 for the handling and transportation of an eyeball according to the present invention has a base body 2 comprising a first housing seat or cavity 4 for housing at least partially an eyeball 1, at least one retaining element 3 for retaining the eyeball 1 in the first housing seat or cavity 4 extending around a preferably vertical axis (not shown in the figures), and a lid 5 removably combinable with the base body 2.

In the embodiment shown in figures, the base body 2 is made of two portions, respectively a first upper portion 2a and a lower portion 2b, which are removably combinable through appropriate releasable coupling means.

Alternatively, the base body 2 can be made in one piece without departing from the protective scope of the present invention.

The base body 2 has, in its upper portion 2a, the first housing seat or cavity 4 for housing at least partially an eyeball 1. The first housing seat or cavity 4 is a hollow seat open to the upper part in order to allow the eyeball 1 to be inserted therein.

In the embodiment shown in FIGS. 2 and 4, the housing seat or cavity 4 has a hemispheric shape, but it could have the sphere shape or the shape of a different sphere portion without departing from the protection scope of the present invention.

Alternatively, the first housing seat 4 could have a different shape, for example a cubic, cylindrical or conical shape, or else a portion thereof, but the Applicant believes that the hemispheric shape, or the shape of sphere portion, reduces the number of edges and allows a better transportation of the eyeball 1 without damages or traumas to it.

Referring to FIGS. 1-4, the first housing seat or cavity 4 is open on top and is made so as to have the maximum diameter Dmax at the axially upper portion of the cavity itself.

Preferably, the maximum diameter Dmax is comprised in the range from 15 to 40 mm, still more preferably from 20 to 30 mm.

In its lower portion, the first housing seat or cavity 4 is connected to a second hollow seat 7 for housing the eyeball stump.

Referring to the embodiment shown in FIGS. 2 and 4, the second hollow seat 7 for housing the eyeball stump is also obtained in the upper portion 2a of the base body 2.

The second hollow seat 7 has a cylindrical shape and is provided with a diameter comprised in the range from 0.1 Dmax and 0.7 Dmax.

In the embodiment shown in FIGS. 1-4, the retaining element 3 is like a crown wheel comprising a plurality of fins 13, at least three, radially arranged around the cavity 4.

The fins 13 are shaped to contact the eyeball for at least 15% of an ocular circumference obtained by the intersection between a plane orthogonal of the cavity 4 and the eyeball itself.

In fact, the Applicant observed that the fins 13 must contact the eyeball and such a contact must happen for at least a significant portion of the eyeball itself in order to assure the eyeball to be kept in position as some operations are carried out, such as the transportation, the positioning under a microscope, the sclerocorneal cutting, and other processing types in the research scope, for example.

Preferably for such a purpose, the fins 13 are shaped so as to contact the eyeball for at least 40% of an ocular circumference, still more preferably the fins 13 are shaped so as to contact the eyeball for at least 70% of an ocular circumference. The fins 13 are angularly spaced and extend from an annular element 14 arranged around the cavity 4. In detail, the annular element 14 extends circumferentially around a radially outer surface of the base body 2.

The retaining element 3 is removably coupled through convenient releasable coupling means 18 which can be adjusted selectively to the base body 2.

A thread 18a on the base body, adapted to engage with a corresponding reverse thread 18b provided on a radially inner surface of the retaining element 3, can stand for the coupling means 18.

In detail, the reverse thread 18b is provided on an inner surface of the annular element 14.

The fins 13 has each a free end, the free ends 13a are arranged along a circumference having a diameter smaller than Dmax of the housing cavity 4 in order to abut and retain the eyeball 1 in the housing cavity 4.

Preferably, the fins 13 of said retaining element 3 are elastically deformable.

The elasticity of the fins 13 allows the eyeball 1 to be retained in the housing cavity 4 without damaging it in case of sudden movements.

Still in order to not damage the eyeball during the transportation or handling, the free end 13a of the fins 13 is folded upwards, referring to figures.

Alternatively, the free end 13a of the fins 13 could be folded downwards without departing from the protective scope of the present invention.

The screwing of the thread 18a on the reverse thread 18b lowers the retaining element on the base body 2 in an axial direction, thereby reducing the space in which the eyeball 1 is retained.

On the contrary, the unscrewing of the thread 18a on the reverse thread 18b raises the retaining element 3 on the base body 2 in an axial direction, thereby increasing the space in which the eyeball 1 is retained.

In other terms, by acting on the first coupling means 18, an adjustment of the retaining element 3 is allowed in the axial direction with respect to the eyeball 1.

In this way it is possible to adapt the coupling between the retaining element 3 and the housing cavity 4 to the actual size of the eyeball 1.

In an alternative embodiment, the sealing of the eyeball 1 can be achieved only by elastic fins 13, in other words without the need of providing releasable and selectively adjustable coupling means 18.

Still according to another not-illustrated embodiment, a snap system for coupling the annular element 14 to the upper portion 2a of the base body 2 can stand for the releasable coupling means 18.

Figure 6:
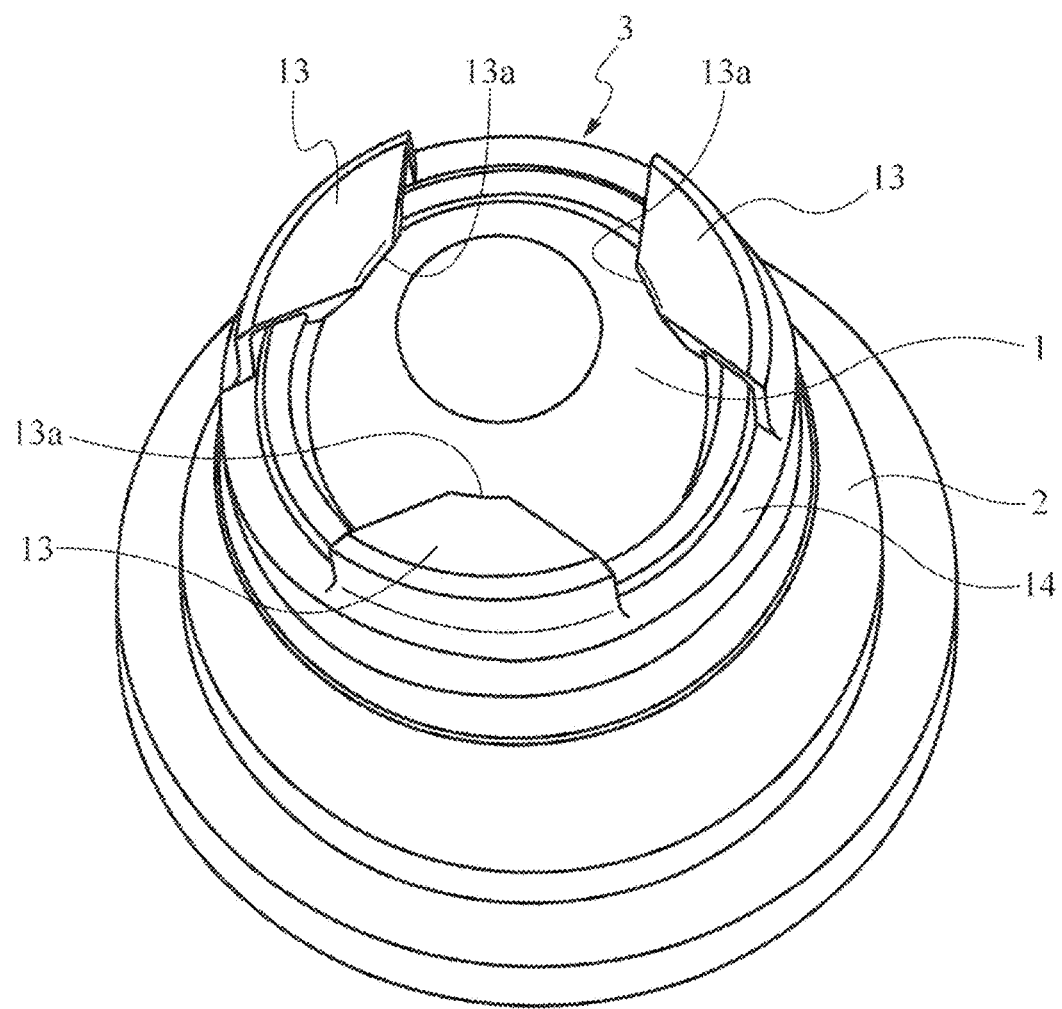
FIG. 6 is a schematic perspective view of an alternative embodiment of the retaining element according to the present invention.

In FIG. 6 another alternative embodiment of the retaining element 3 is shown. According to this embodiment, the retaining element 3 is composed of at least three fins 13 angularly spaced around the first housing seat or cavity 4.

Preferably, the three fins 13 are angularly spaced by an angle greater than 60°, preferably an angle greater than 90°, for example of about 120°.

The three fins 13 extend from an annular element 14 arranged around the housing seat or cavity 4. In detail, the annular element 14 extends circumferentially around a radially outer surface of the base body 2.

Each fin 13 is shaped to contact the eyeball for at least 10% of an ocular circumference obtained by the intersection between a plane orthogonal to the vertical axis of the first housing seat or cavity 4 and the eyeball itself.

Also in this case, the retaining element 3 can be removably coupled through convenient releasable coupling means 18 which can be adjusted selectively to the base body 2.

Figure 7:
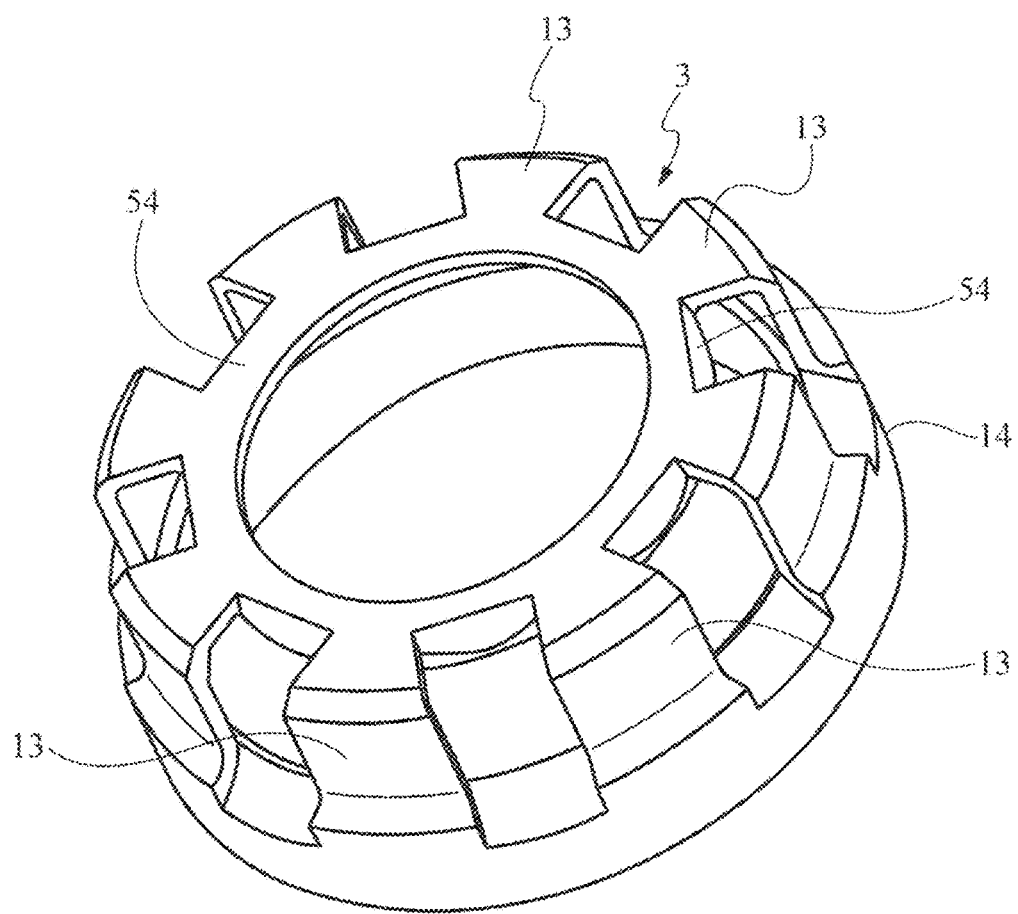
FIG. 7 is a schematic perspective view of an alternative embodiment of the retaining element according to the present invention.

In FIG. 7 another alternative embodiment of the retaining element 3 is shown. According to this embodiment, the retaining element 3 is composed of a plurality of fins 13, preferably eight, angularly spaced around the first housing seat or cavity 4.

The fins 13 are joined by an upper annular element adapted to contact the eyeball 1.

In this case, since the annular element 54 is sprung due to elasticity or flexibility of the fins 13, a precise sealing of the eyeball is allowed during the cutting operations of the cornea.

As better shown in figures, the device has a lid 5 removably combinable with the base body 2.

The lid 5 is shaped so that, once combined with the base body 2, it makes a cavity 8 for a preservation and/or transportation liquid.

In the embodiment shown in figures, the cavity 8 for the preservation and/or transportation liquid is shaped so that the eyeball 1 is immersed at least partially in the liquid, preferably completely immersed in the liquid.

Preferably, the cavity 8 comprises a volume between 10 and 100 milliliters.

For this purpose, in the embodiment shown in FIGS. 1-4, the lid 5 is shape like a substantially cylindrical overturned glass, which is provided with a side surface 9 and a bottom 10.

The bottom has a central opening 11 and a plug 12. An O-ring can be mounted on the plug 12 for the watertightness.

The opening 11, which in the embodiment shown in FIGS. 1, 2, 4 is circular, allows the outside of the device to be fluidically communicated with the cavity 8 so that to be able to feed the cavity 8 with a convenient preservation and/or transportation liquid.

The lid 5 is combined with the base body 2 by second releasable coupling means 28, in other terms means allowing the lid to be fixed and removed from the base body 2.

In the embodiment shown in figures, a thread 28a is provided as releasable coupling means 28 to combine the lid 5 with the base body 2, the thread being provided on a radially inner surface of the side surface 9, and a reverse thread 28b is provided on a radially outer surface of the base body 2, preferably on a radially outer surface of the lower portion 2b of the base body 2.

Anyway, different releasable coupling means can be provided without departing from the protection scope of the present invention.

The coupling between the lid 5 and the base body 2 is such to guarantee a hermetic seal of the lid 5 on the base body 2 so that the liquid contained in the cavity 8 cannot leak.

For this purpose, a sealing element 15 is provided between the outer surface of the base body 2 and the receptacle 5, such as an O-ring arranged in an annular seat 16 provided in the radially outer surface of the base body and, in particular, on the radially outer surface of the lower portion 2b of the base body 2.

In FIG. 4 the device 100 according to the present invention is shown and provided with an additional piece with respect to FIG. 2, in particular a ring nut 20 removably combinable with the base body 2.

Figure 5:
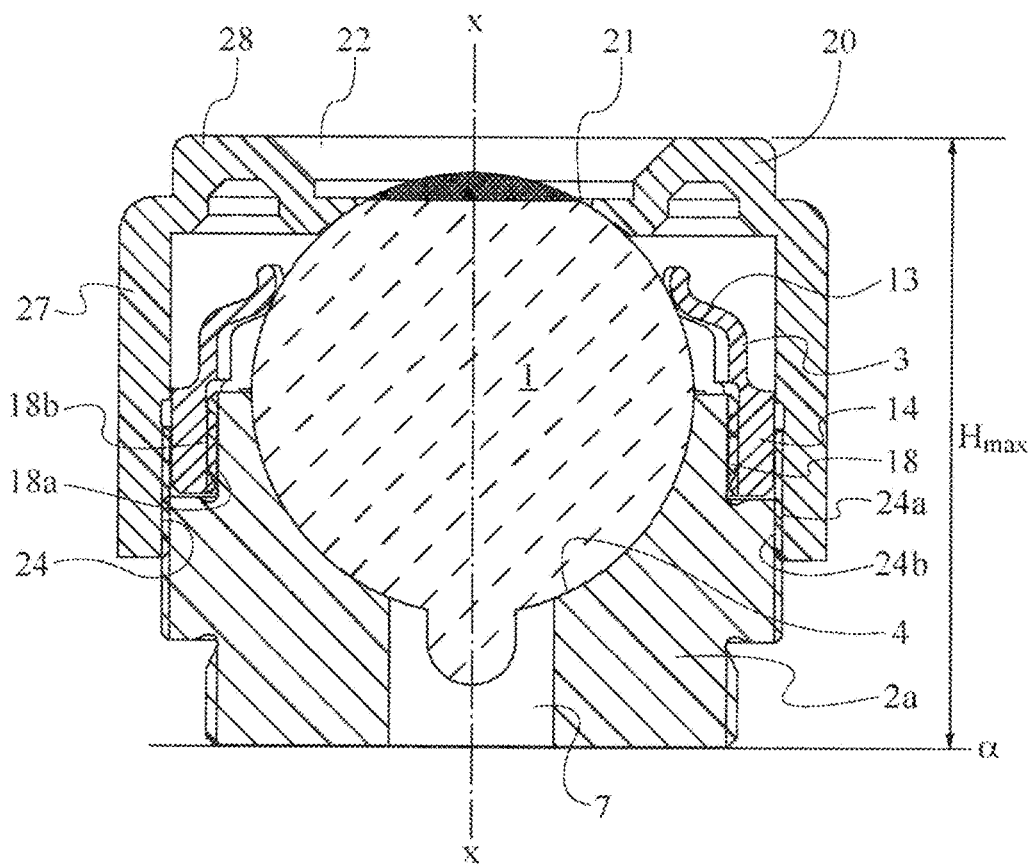
FIG. 5 is a schematic sectional view of the ring nut and the upper portion of the base body, coupled one to another to form a receptacle for the eyeball adapted to allow the microscope observation.

In detail, by combining the ring nut 20 with the upper portion 2a of the base body and removing the upper portion from the base body 2, a receptacle 100 holding the eyeball 1 is obtained, which is shaped for the microscope observation of the endothelium, better shown in FIG. 5.

For this purpose, the ring nut 20 has fastening means 24 releasable from the upper portion 2a of the base body 2.

A thread 24a, couplable with a corresponding reverse thread 24b provided on a side surface of the upper portion 2a of the base body 2, stands for the releasable fastening means 24.

Once the ring nut and the upper portion 2a of the base body have been combined with the upper portion 2a of the base body 2, they have a maximum height Hmax measured from a plane a containing the bottom surface of the upper portion 2a of the base body 2.

The ring nut 20 comprises a substantially circular opening 21 for housing at least a portion of the eyeball 1 containing the cornea.

In detail, the ring nut 20 is shaped like an overturned glass and comprises a cylindrical side surface 27 and a bottom surface 28, which is shown in figures as facing upwards.

The circular opening 21 is provided centrally in the bottom surface 28 and is sized to house the portion of the eyeball containing the cornea.

The bottom surface 28 is lowered with respect to the upper end of the side surface 27 so that to form an upper tank 22 for an observation liquid.

Advantageously, the device according to the present invention can have means 23 for fastening said base body 2 to a bearing surface, such as a table or a working surface.

In the embodiment shown in figures, a double-sided adhesive is provided as means 23 for fastening said base body 2 to a bearing surface.

The double-sided adhesive extends preferably for the whole bottom surface of the base body 2 and is integral thereto.

At the other end, the double-sided adhesive can become also integral with a bearing surface by removing a not-shown peelable flap.

The presence of the constraining means 23 for fastening said base body 2 to a bearing surface is particularly advantageous during the cornea cutting.

Other elements can be provided as constraining means 23, such as Velcro portions or velvet or fabric portions, or else a suction pad, without departing from the protection scope of the present invention.

The present invention has been described referring to some embodiments. To the embodiments herein represented in detail various modifications can be made, anyway remaining in the protection scope of the invention, defined by the following claims.

The invention claimed is:

1. A device (10) for the handling and transportation of an eyeball, comprising:
   a base body (2) comprised of a first housing seat or cavity (4) that extends around a substantially vertical axis and is configured for housing at least partially an eyeball (1);
   a retaining element (3) for retaining the eyeball (1) in said first housing seat or cavity (4), said retaining element (3) comprised of at least three fins (13) arranged around said first housing seat or cavity (4),
   said fins being shaped so as to contact the eyeball for at least 15% of an ocular circumference obtained by an intersection between a plane orthogonal to the vertical axis of said first housing seat or cavity (4) and the eyeball itself; and
   at least one lid (5) removably mountable upon the base body (2), the lid (5) comprised of a top portion and a side portion extending laterally from a periphery of the top portion, the side portion and the top portion together forming a cavity (8) within an interior of the lid (5), and a terminal end of the side portion located opposite the top portion forming a coupling zone for coupling with the base body (2), the lid (5) and the base body (2), when combined, forming a chamber that completely encloses said eyeball therein, the fins (13) of said retaining element (3) being elastically deformable, and said retaining element (3) is mounted to said base body (2) by way of a releasable coupling means (18) that permits adjustment of a position of the retaining element (3) on the base body (2) in an axial direction with respect to the eyeball.

2. The device (10) for the handling and transportation of an eyeball according to claim 1, wherein said fins (13) are shaped so as to contact the eyeball for at least 40% of said ocular circumference.

3. The device (10) for the handling and transportation of an eyeball according to claim 1, wherein said base body (2) further comprises a second seat (7) in communication with said first housing seat or cavity (4), said second seat (7) being configured to accommodate a stump of a visual nerve of the eyeball (1).

4. The device (10) for the handling and transportation of an eyeball according to claim 3, wherein said second seat (7) is located at a bottom end of said first housing seat or cavity (4).

5. The device (10) for the handling and transportation of an eyeball according to claim 1, wherein said retaining element (3) is removably fastened to said base body (2) through first releasable coupling means.

6. The device (10) for the handling and transportation of an eyeball according to claim 1,
wherein said first housing seat or cavity (4) comprises a maximum diameter Dmax, and
wherein said retaining element (3) comprises at least two portions arranged for defining a diameter shorter than said maximum diameter Dmax of said first housing seat or cavity (4).

7. The device (10) for the handling and transportation of an eyeball according to claim 1, wherein said lid (5) combined with said base body (2) form a cavity (8) for a preservation and/or transportation liquid.

8. The device (10) for the handling and transportation of an eyeball according to claim 1, wherein said lid (5) is combinable with said base body (2) by way of a second releasable coupling means that releasably couples the coupling zone of the lid (5) to the base body (2).

9. The device (10) for the handling and transportation of an eyeball according to claim 1, wherein the cavity (8) for a preservation and/or transportation liquid is hermetically sealed.

10. The device (10) for the handling and transportation of an eyeball according to claim 1, wherein the top portion of said lid (5) comprises an opening (11) for fluidic communication of said cavity (8) with an exterior of the device, and at least one plug (12) configured to close the opening (11) hermetically and removably.

11. The device (10) for the handling and transportation of an eyeball according to claim 1, wherein a volume of said cavity (8) is between 10 and 100 milliliters.

12. The device (10) for the handling and transportation of an eyeball according to claim 1, wherein said first housing seat or cavity (4) has any of a sphere shape, a sphere-portion shape, and a conical shape.

13. The device (10) for the handling and transportation of an eyeball according to claim 1, wherein said base body (2) is composed of an upper portion (2a) and a lower portion (2b), said upper portion (2a) and said lower portion (2b) being removably combinable with each other.

14. The device (10) for the handling and transportation of an eyeball (1) according to claim 1, further comprising:
constraining means (23) for fastening said base body to a bearing surface.

15. The device (10) for the handling and transportation of an eyeball (1) according to claim 1, wherein said retaining element (3) comprises a crown wheel, which includes a plurality of fins that are circumferentially arranged around said first housing seat or cavity (4) for housing at least partially said eyeball (1).

16. The device (10) for the handling and transportation of an eyeball (1) according to claim 1, wherein said retaining element (3) comprises an annular contacting element (54) adapted to join said fins (13) and to contact the eyeball.

17. The device (10) for the handling and transportation of an eyeball (1) according to claim 1,
wherein the first housing seat or cavity (4) is formed as a hemispherical depression penetrating downward into a thickness of the base body (2) for receiving at least partially a lower part of the eyeball (1), and
wherein the fins of the retaining element (3) extend upward in a direction opposite that of the depression so as to make contact with an upper part of the eyeball exposed outside the hemispherical depression of the first housing seat or cavity (4).

18. The device (10) for the handling and transportation of an eyeball (1) according to claim 17, wherein a bottom of the hemispherical depression of the first housing seat or cavity (4) opens into a second hollow seat (7) extending into the thickness of the base body (2) and in communication with the hemispherical depression, the second hollow seat (7) having a width (D) sufficient to receive a stump of the eyeball (1).

19. A device (10) for the handling and transportation of an eyeball (1) comprising:
a base body (2) comprised of a first housing seat or cavity (4) that extends around a substantially vertical axis and is configured for housing at least partially an eyeball (1);
a retaining element (3) for retaining the eyeball (1) in said first housing seat or cavity (4), said retaining element (3) comprised of at least three fins (13) arranged around said first housing seat or cavity (4),
said fins being shaped so as to contact the eyeball for at least 15% of an ocular circumference obtained by an intersection between a plane orthogonal to the vertical axis of said first housing seat or cavity (4) and the eyeball itself;
at least one lid (5) removably mountable upon the base body (2), the lid (5) comprised of a top portion and a side portion extending laterally from a periphery of the top portion, the side portion and the top portion together forming a cavity (8) within an interior of the lid (5), and a terminal end of the side portion located opposite the top portion forming a coupling zone for coupling with the base body (2),
the lid (5) and the base body (2), when combined, forming a chamber that completely encloses said eyeball therein; and
a ring nut (20), having formed therein a hole (21) for housing at least one portion of the eyeball (1) containing the cornea,
said ring nut (20) being removably combinable with said base body (2).

20. The device (10) for the handling and transportation of an eyeball (1) according to claim 19, wherein said ring nut (20) comprises removable fastening means (24) for the fastening to said base body (2), and at least one tank (22) for an observation liquid, said tank having a shape adapted to house at least partially the cornea.

21. The device (10) for the handling and transportation of an eyeball (1) according to claim 20,
- wherein said base body (2) is composed of an upper portion (2a) and a lower portion (2b), said upper portion (2a) and said lower portion (2b) being removably combinable with each other, and
- wherein said ring nut (20) is combinable with said upper portion (2a) of said base body (2) through said removable fastening means (24).

22. The device (10) for the handling and transportation of an eyeball (1) according to claim 19, wherein said ring nut (20) combined with said upper portion (2a) of said base body (2) has a maximum height (Hmax) lower or equal to 50 mm.

* * * * *